US006158484A

United States Patent [19]
Greenlee

[11] Patent Number: 6,158,484
[45] Date of Patent: Dec. 12, 2000

[54] DISPENSER FOR CHURCH COMMUNION LIQUID

[76] Inventor: Wilfred E. Greenlee, 4423 Eagles Cove Ct., Louisville, Ky. 40241

[21] Appl. No.: 09/450,161

[22] Filed: Nov. 29, 1999

Related U.S. Application Data
[60] Provisional application No. 60/123,044, Mar. 5, 1999.

[51] Int. Cl.⁷ ....................................................... B65B 1/04
[52] U.S. Cl. ........................... 141/242; 141/247; 222/330
[58] Field of Search .............................. 141/18, 234, 237, 141/247, 242, 243; 222/330, 506

[56] References Cited

U.S. PATENT DOCUMENTS 1,202,439  10/1916  Scott .
1,709,771   4/1929  Brady .
4,453,576   6/1984  Burns ........................................ 141/168
4,844,298   7/1989  Ohoka et al. .............................. 222/58

Primary Examiner—Steven O. Douglas
Attorney, Agent, or Firm—Stites & Harbison, PLLC; David W. Nagle, Jr.; Vance A. Smith

[57] ABSTRACT

A dispenser made in accordance with the present disclosure includes a liquid storage container and a mechanical regulating assembly that are mounted on a frame. A plurality of conduits is in liquid communication with the storage container and dispenses liquid flowing from the container under the force of gravity through the conduits through open distal ends. The regulating assembly of the dispenser regulates this flow using two pinch rollers that are moveable between a closed position, wherein the rollers pinch the sections of tubing and restrict flow, and an open position, wherein there is a free flow of liquid through the sections of tubing.

14 Claims, 4 Drawing Sheets

6,158,484

DISPENSER FOR CHURCH COMMUNION LIQUID

BACKGROUND OF THE INVENTION

This application claims priority from U.S. provisional application No. 60/123,044 filed on Mar. 5, 1999.

The present invention relates to a dispenser for filling multiple receptacles, and, more particularly, to a dispenser that simultaneously fills a plurality of drinking cups that are arranged in a predetermined pattern on a serving tray.

Communion is a commonly practiced ritual of Christian churches. During communion, church members are provided with and drink juice or wine in commemoration of the Last Supper of Jesus Christ. In distributing the communion juice or wine, many churches use communion trays that have an insert holding a plurality of small drinking cups. A typical tray can hold up to forty drinking cups. Even though these trays facilitate distribution of the communion juice or wine, it is still very time consuming to fill the individual drinking cups. This problem is especially severe in churches with large congregations. For example, Southeast Christian Church in Louisville, Ky. has approximately 14,000 members. Filling the drinking cups needed for weekend services requires nearly 30 man-hours of labor.

It is therefore a primary object of the present invention to provide a dispenser that can simultaneously fill a plurality of drinking cups.

It is another object of the present invention to provide a dispenser that fills each cup with a precise amount of liquid.

It is still another object of the present invention to provide a dispenser that requires little maintenance or cleaning.

These and other objects and advantages of the present invention will become apparent upon a reading of the following description.

SUMMARY OF THE INVENTION

The dispenser of the present invention includes a liquid storage container and a mechanical regulating assembly that are mounted on a frame. This frame also supports a lower plate that is positioned below the liquid storage container and the mechanical regulating assembly, said lower plate defining a plurality of openings. These openings are arranged such that a corresponding tray of smaller volume receptacles can be positioned below the lower plate and in registry with the openings. Furthermore, each such opening is equipped with a fitting that connects the opening to a section of plastic tubing. The opposite ends of the sections of plastic tubing are connected to and are in liquid communication with the liquid storage container. Thus, if no obstructions or hindrances were interposed between the liquid storage container and the lower plate, liquid stored in the container would flow freely under the force of gravity through the various sections of plastic tubing and out through the openings in the lower plate for dispensing into the receptacles positioned below the lower plate. The mechanical regulating assembly of this invention, however, regulates this flow. More specifically, the regulating assembly of the present invention includes two pinch rollers that are moveable between a closed position, wherein the rollers pinch the sections of tubing and restrict flow, and an open position, wherein there is a free flow of liquid through the sections of tubing.

DESCRIPTION OF THE PREFERRED EMBODIMENTS

Figure 1:
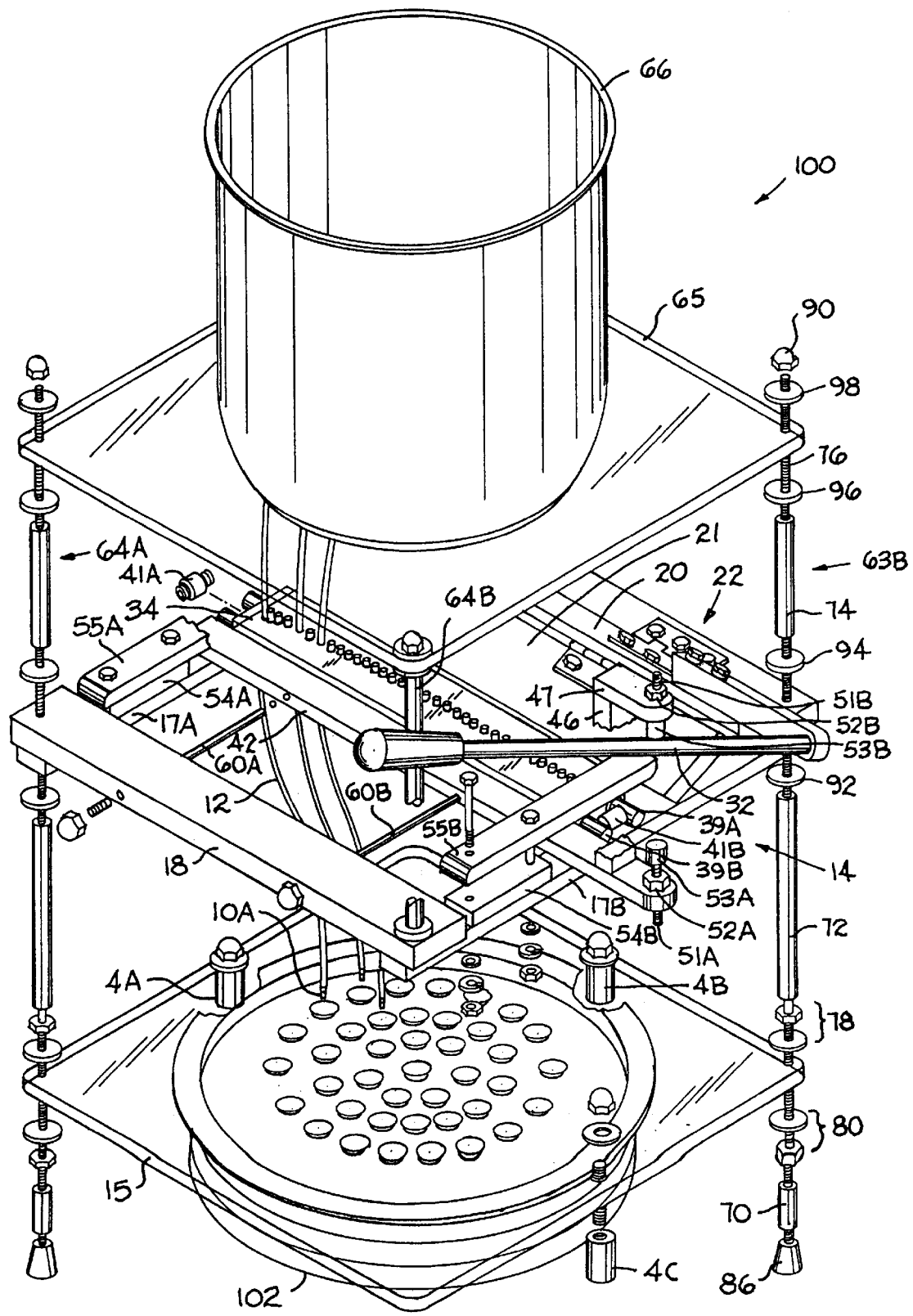
FIG. 1 is a exploded perspective view of a preferred embodiment of the dispenser of the present invention.
Figure 2:
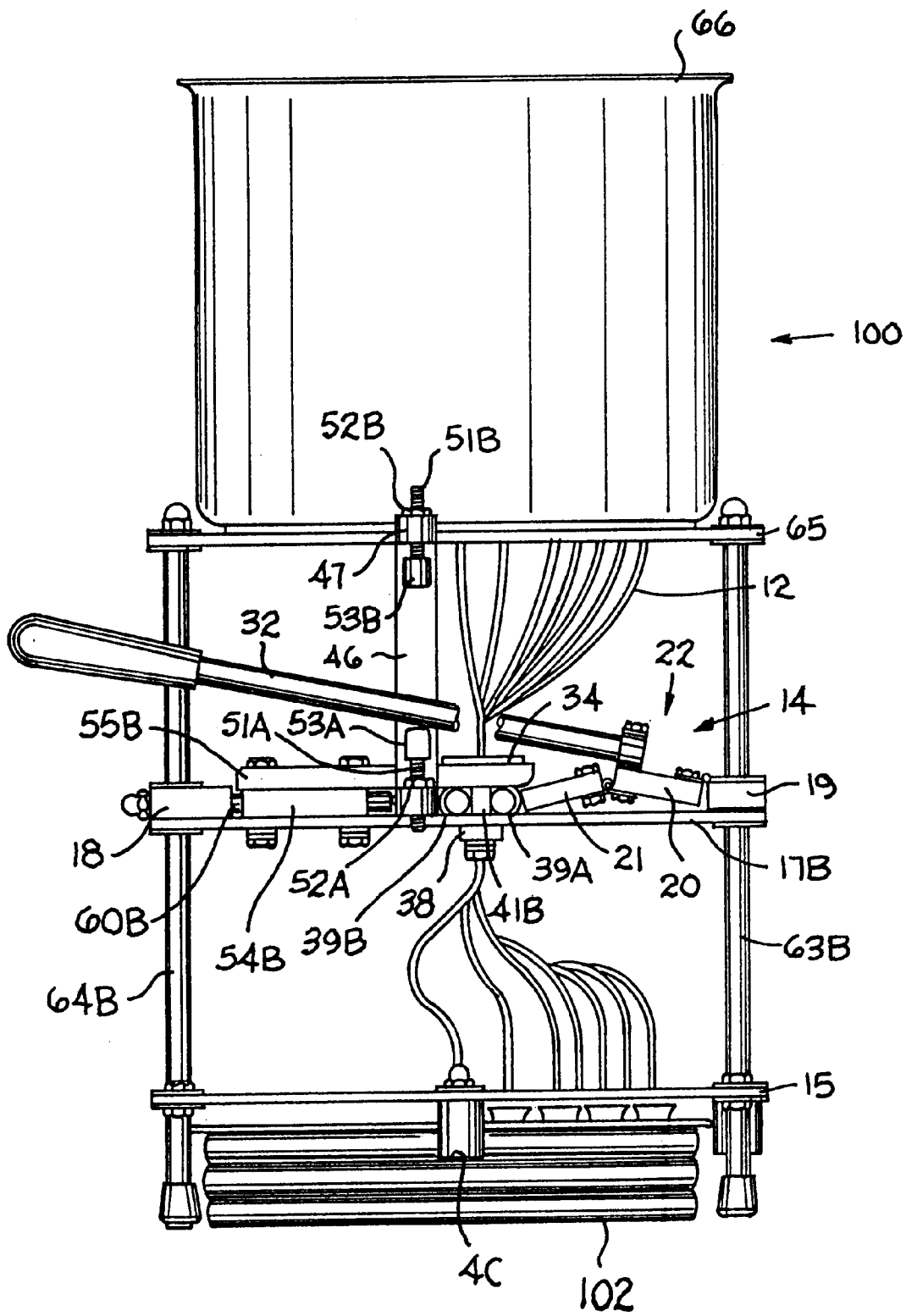
FIG. 2 is a side view of the dispenser of FIG. 1.
Figure 3:
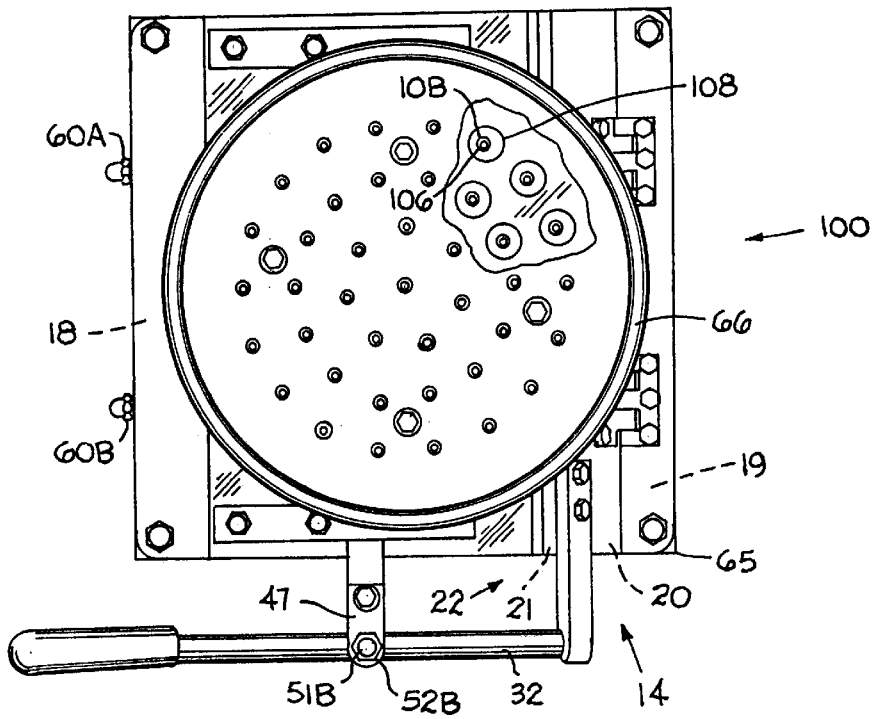
FIG. 3 is a top view of the dispenser of FIG. 1.

As shown in FIGS. 1–3, the dispenser 100 of the present invention includes a liquid storage container 66, preferably a 24-quart stainless steel pot that is mounted on a frame.

This frame is comprised of two front vertical support rod assemblies 64A, 64B and two rear vertical support rod assemblies 63A, 63B. These assemblies 64A, 64B, 63A, 63B cooperate to support a lower plate 15, a pot mounting plate 65, and a mechanical regulating assembly (generally indicated by reference numeral 14). In this preferred embodiment, both the lower plate 15 and the pot mounting plate 65 are constructed of a transparent resinous material, preferably Plexiglas® manufactured by the Rohm and Haas Company of Philadelphia, Pa.

Referring now to the exploded view of FIG. 1, each vertical support rod assembly comprises multiple sections of steel tubing disposed on a threaded rod 76 that spans the height of the dispenser 10. The sections of steel tubing serve as spacers separating the various levels of the dispenser 10. For example, with reference to the rear vertical support assembly 63B, a lower section of steel tubing 70 serves to space the lower plate 15 from the underlying support surface. A second, intermediate section of tubing 72 serves to space the mechanical regulating assembly 14 from the lower plate 15, and a third, upper section of tubing 74 serves to space the mechanical regulating assembly 14 from the pot mounting plate 65. The threaded rod 76 is secured with respect to the lower plate 15 by a pair of nut and washer arrangements 78, 80 abutting the upper and lower surfaces of the lower plate 15. And, the threaded rod 76 is preferably capped at its upper end with a crowned nut 90. Lastly, a foot 86 is attached to the threaded rod 76 at the bottom end thereof for providing stable support for the dispenser 10 upon the underlying support surface. As shown in FIG. 1, it is contemplated that washers 92, 94, 96, 98 may also be used to prevent the sections of tubing from contacting the support structure of the mechanical regulating assembly 14 and the pot mounting plate 65. Each of the other vertical support rod assemblies 63A, 64A, 64B is similarly constructed. Regardless, the vertical support rod assemblies 63A, 63B, 64A, 64B serve only to define the frame of the dispenser 100 of the present invention; thus, substantial modifications or changes could be made to these support assemblies without departing from the spirit and scope of the present invention.

Figure 6:
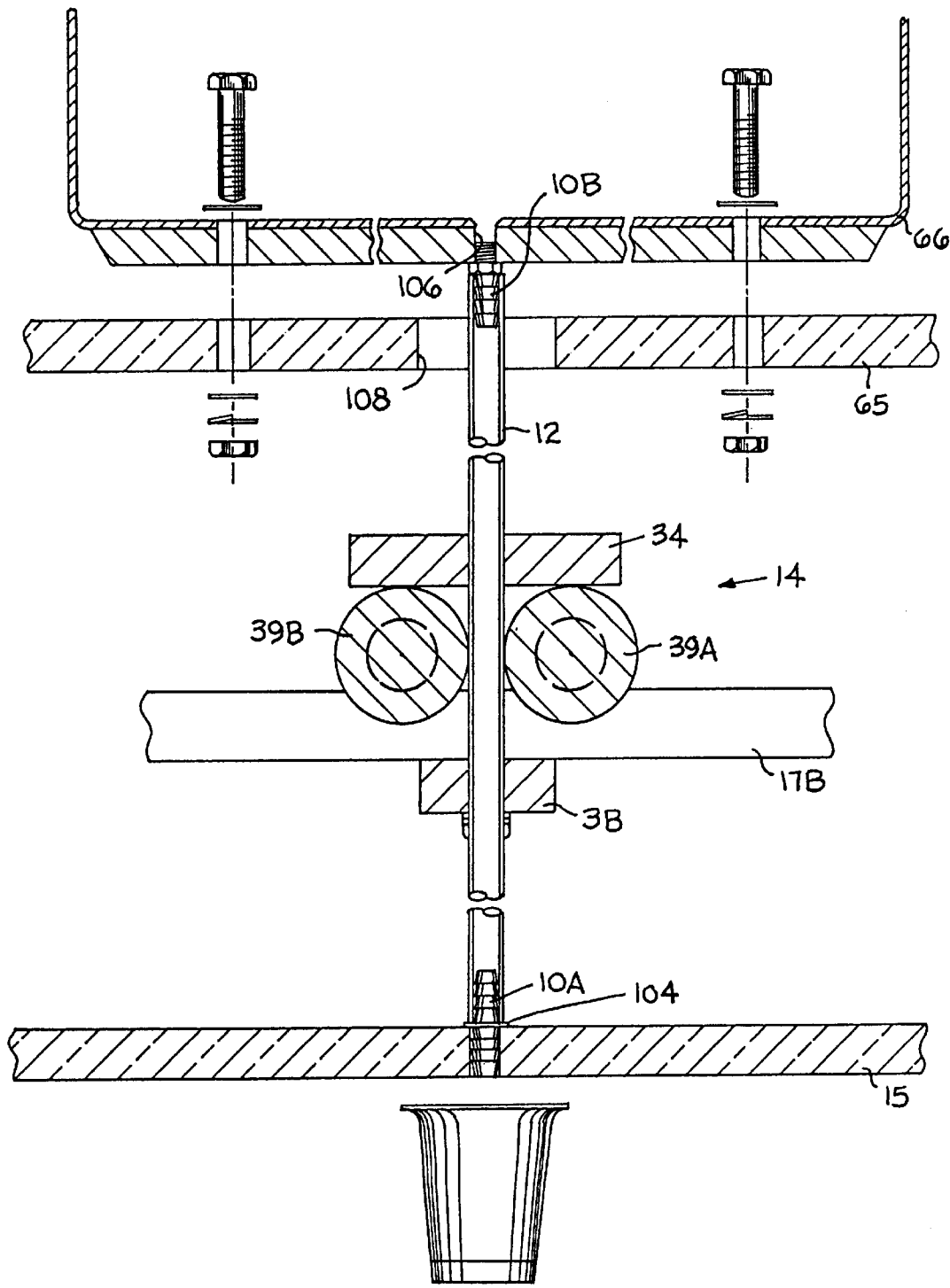
FIG. 6 is an exploded side sectional view of a portion of the regulating assembly of the dispenser of FIG. 1.

The lower plate 15 separates the preferred dispenser 100 from a tray 102 of receptacles (e.g., drinking cups) that is to be filled. And, the lower plate 15 defines a plurality of openings 104, as shown in FIG. 6. In this preferred embodiment, the lower plate 15 defines forty such openings 104. These openings are arranged such that a corresponding tray 102 of forty drinking cups can be positioned below the lower plate 15 and in registry with the openings 104. To assist in properly positioning a tray 102 below the lower plate 15, the dispenser has three stops 4A, 4B, 4C that are mounted to the lower plate 15 and extend downwardly to define an area for receiving the tray 102, as shown in FIGS.

1 and 2. Once positioned between the stops 4A, 4B, 4C, the tray 102 is rotated until an identification mark (not shown) imprinted on the tray 102 is aligned with a similar mark (not shown) on the lower plate 15, thus aligning the tray 102, and the drinking cups, radially with the openings 104 defined by the lower plate 15.

Referring now to the side sectional view of FIG. 6, each opening 104 defined by the lower plate 15 is equipped with a fitting 10A (preferably a stainless steel dental fitting) that connects the opening 104 to a section of plastic tubing 12, preferably food-grade Tygon® tubing, manufactured by Norton Performance Plastics of Akron, Ohio. The preferred Tygon® tubing has an outer diameter of ¼" and an inner diameter of ⅛", although other dimensions may be used without departing from the spirit and scope of the present invention. These sections of tubing are the conduits that carry liquid stored in the pot 66 through the regulating assembly 14 (as will be described in further detail below) and into the individual drinking cups.

The pot 66 that stores the liquid is bolted (as depicted in FIG. 6) or similarly mounted to the pot mounting plate 65 at the top of the dispenser 100. As best shown in the top view of FIG. 3, the pot 66 and the pot mounting plate 65 define a plurality of corresponding openings 106, 108, the number of openings 106, 108 being equal to the number of drinking cups to be filled. As best shown in FIG. 6, each of these openings 106, 108 is also provided with a fitting 10B (preferably a stainless steel dental fitting) to which the opposite end of one of the above-described sections of plastic tubing 12 is connected. Thus, if no obstructions or hindrances are interposed between the pot mounting plate 65 and the lower plate 15, liquid stored in the pot 66 would flow freely under the force of gravity from the pot 66, through the various sections of plastic tubing 12, and out the openings 104 in the lower plate 15 for dispensing into the drinking cups positioned below the lower plate 15.

However, it is clearly desired that the flow of liquid from the pot 66 to the individual drinking cups be regulated in some manner. Thus, the present invention incorporates a regulating assembly 14 that generally comprises two pinch rollers 39A, 39B that are moveable between a closed position, wherein the rollers 39A, 39B pinch the sections of tubing 12, thereby restricting flow of liquid through the sections of tubing 12, and an open position, wherein the rollers 39A, 39B permit free flow of liquid through the sections of tubing 12.

As mentioned above, the regulating assembly 14 is interposed between the pot mounting plate 65 and the lower plate 15. A front bar 18, a rear bar 19, and two side bars 17A, 17B provide a support structure for the mounting of the components of the regulating assembly 14. As best shown in the exploded view of FIG. 1, these support bars 18, 19, 17A, 17B are held in a position intermediate the lower plate 15 and the pot mounting plate 65 through attachment to the front and rear vertical support rod assemblies 64A, 64B, 63A, 63B. Furthermore, it is preferred that the front bar 18, rear bar 19, and two side bars 17A, 17B be arranged in a generally rectangular configuration.

As shown in FIGS. 1, 2 and 4–6, the pinch rollers 39A, 39B have reduced diameter ends that rest upon and are supported by the side bars 17A, 17B. To prevent the pinch rollers 39A, 39B from lifting away from the side bars 17A, 17B, a pair of retainer bars 55A, 55B is used. The retainer bars 55A, 55B are bolted or similarly secured to the side bars 17A, 17B and maintained at a spaced vertical distance from the side bars 17A, 17B by a pair of corresponding spacer bars 54A, 54B. The retainer bars 55A, 55B extend beyond the spacer bars 54A, 54B and are adapted to contact the upper surfaces of the reduced diameter ends of the pinch rollers 39A, 39B.

Movement of the pinch rollers 39A, 39B toward the front of the dispenser 100 is restricted by an adjustment bar 42. This adjustment bar 42 lies parallel to the front and rear support bars 18, 19, and is secured between the side bars 17A, 17B and the associated retainer bars 55A, 55B. Movement of the pinch rollers 39A, 39B toward the rear of the dispenser 100 is restricted by a toggle arrangement that moves the pinch rollers 39A, 39B between the open and closed positions, as will be described in further detail below.

To guide the individual sections of tubing 12 through the pinch rollers 39A, 39B, the regulating assembly 14 includes upper and lower tubing locator bars 34, 38 which are spaced at a predetermined vertical distance above and below the pinch rollers 39A, 39B. The upper tubing locator bar 34 is held between the aforementioned retainer bars 55A, 55B above the pinch rollers 39A, 39B. The lower tubing bar 38 is bolted or similarly secured to the side bars 17A, 17B and is positioned below the pinch rollers 39A, 39B. Each of these tubing locator bars 34, 38 defines a plurality of openings arranged along a common axis. The individual sections of tubing 12 pass through the openings defined by the upper tubing locator bar 38, between the pinch rollers 39A, 39B, and through the lower tubing locator bar 34.

Figure 4:
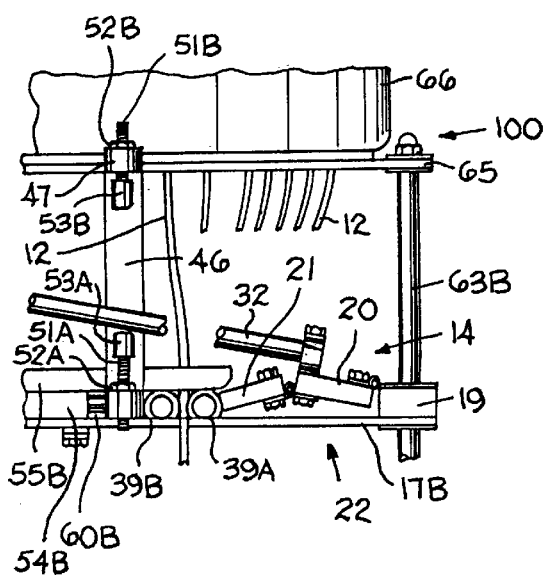
FIG. 4 is a partial side view of the dispenser of FIG. 1 with the regulating assembly in a closed position.
Figure 5:
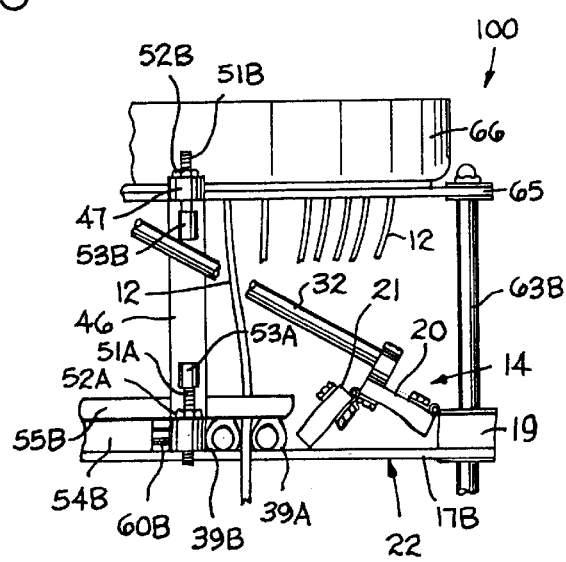
FIG. 5 is a partial side view of the dispenser of FIG. 1 with the regulating assembly in an open position.

As stated, the pinch rollers 39A, 39B are moveable between a closed position, wherein the rollers 39A, 39B pinch the sections of tubing 12, thereby restricting flow of liquid through the sections of tubing 12, and an open position, wherein the rollers 39A, 39B permit free flow of liquid through the sections of tubing 12. The regulating assembly 14 includes a toggle arrangement for moving the pinch rollers 39A, 39B between the closed and open positions. This toggle arrangement is essentially comprised of a hinge 22 that has a front section 21 and a rear section 20. The rear section of this hinge 20 is itself hinged to the rear bar 19, and the front section 21 of the hinge 22 is adapted to abut the rearmost pinch roller 39A. A handle 32 is bolted or similarly secured to the rear section 20 of the hinge 22. By rotating the handle 32 downward (counterclockwise), a force is applied to the rear section 21 of the hinge 22, forcing the hinge 22 closed. This closing of the hinge 22 applies a lateral force to the rearmost roller 39A, causing it to move toward the other substantially fixed pinch roller 39B, thereby pinching the sections of tubing 12 closed, as shown in FIG. 4. Once the handle 32 is rotated upwardly (clockwise), springs 41A, 41B (shown in FIG. 1) positioned at the ends of the pinch rollers 39A, 39B return the roller 39A to an open position, as shown in FIG. 5.

As an added feature and as shown in FIGS. 1–5, in this preferred embodiment, the aforementioned adjustment bar 42 extends outwardly past the side bar 17B. The distal end of the adjustment bar 42 defines an opening for accommodating a substantially vertical bolt 51A. A corresponding nut 52A is fixed to the adjustment bar 42 in registry with the opening therein. The bolt 51A is threaded through the nut 52A) extends upwardly from the adjustment bar 42, and is capped with a rubber stopper 53A. By turning the bolt 51A relative to the nut 52A, the position of the stopper 53A relative to the adjustment bar 42 can be fixed such that, when the handle 32 contacts this lower stopper 53A, the pinch rollers 39A, 39B are in the closed position.

Furthermore, a support 47 is spaced a vertical distance from the adjustment bar 42 by vertical spacer 46 welded or similarly secured to the adjustment bar 42 and the support 47. This support 47 similarly defines an opening for accommodating a substantially vertical bolt 51 B. A corresponding nut 52B is fixed to the support 47 in registry with the opening therein. This bolt 51 B is threaded through the nut 52B, extends downwardly from the support 47, and is capped with a second rubber stopper 53B. By turning the bolt 51B relative to the nut 52B, the position of the stopper 53B relative to the support 47 can be fixed such that, when the handle 32 contacts this upper stopper 53B, the pinch rollers 39A, 39B are in the open position.

Finally, to ensure that all of the sections of tubing 12 are equally compressed and completely sealed in the closed position, the regulating assembly 14 of the dispenser 100 is preferably equipped with two adjustment rods 60A, 60B that are threaded through the front bar 18, pass through the adjustment bar 42, and extend to and abut the frontmost pinch roller 39B. Clockwise rotation of these rods 60A, 60B thus causes the adjustment rods 60A, 60B to press against the frontmost pinch roller 39B, adjusting its position relative to the second pinch roller 39A. Such adjustment may be needed after repeated use of the dispenser 100 to prevent dripping that results when the rollers 39A, 39B do not adequately pinch the tubes 12 closed.

In practice, while the regulating assembly 14 is in a closed position, an operator slides a tray 102 of drinking cups underneath the lower plate 15 of the dispenser 100. The operator aligns the tray 102 so that the cups are in registry with the openings defined by the lower plate 15. The operator then rotates the handle 32 of the dispenser 100 upwardly, thereby allowing liquid to flow through the sections of tubing 12 and into the drinking cups. When the cups are full, the operator rotates the handle 32 to a closed position, stopping the flow of liquid through the sections of tubing 12. The tray 102 is removed, and another empty tray 102 is moved into position for filling. Whereas manual filling of 250 trays required approximately twenty-one man-hours of labor, the dispenser of the present invention allows an operator to fill 250 trays in just over one hour.

It will be obvious to those skilled in the art that modifications may be made to the preferred embodiments described herein without departing from the spirit and scope of the present invention.

What is claimed is:

1. A dispenser for transferring portions of a predetermined volume of liquid into a plurality of smaller volume receptacles, comprising:
   a support frame;
   a container secured to said support frame nearthe top thereof for storing said predetermined volume of liquid;
   a plurality of conduits in liquid communication with said container for transferring portions of the predetermined volume of liquid from said container to said smaller volume receptacles, said conduits each having an open distal end through which a respective portion of the predetermined volume of liquid can be dispensed into one of said receptacles;
   a regulating assembly interposed between said container and said smaller volume receptacles and including first and second pinch rollers between which said plurality of conduits pass, said regulating assembly being manually operable to move said first and second pinch rollers between an open position, wherein said portions of the predetermined volume of liquid can freely flow under the force of gravity through said conduits and into said smaller volume receptacles, and a closed position, wherein said first and second pinch rollers squeeze said conduits closed, thereby restricting the free flow of said portions of the predetermined volume of liquid through said conduits.

2. A dispenser as recited in claim 1, wherein said support frame comprises:
   a pair of front vertical support assemblies, each such assembly having an upper end and a lower end;
   a pair of rear vertical support assemblies, each such assembly having an upper end and a lower end;
   an upper horizontal plate secured to said front and rear vertical support assemblies near the upper ends thereof for supporting said container;
   a lower horizontal plate secured to said front and rear vertical support assemblies near the lower ends thereof; and
   a support structure comprised of a front support bar, a rear support bar, and two side support bars, said support bars being secured to said front and rear vertical support assemblies in a rectangular configuration substantially parallel to and intermediate said upper and lower plates, said support structure adapted to accommodate said regulating assembly.

3. A dispenser as recited in claim 2 wherein said container defines a plurality of openings, and said upper plate defines a corresponding plurality of openings, each of said conduits being associated with one of said openings, each of said conduits extending from said container and passing through the corresponding opening in said upper plate.

4. A dispenser as recited in claim 3 wherein said lower plate defines a plurality of openings, each of said conduits terminating at one of said openings, such that the portions of the predetermined volume of liquid passing through said conduit are dispensed through said lower plate into said receptacles, said receptacles being positioned below said lower plate in registry with the openings defined by said lower plate.

5. A dispenser as recited in claim 4, wherein each of said conduits is a flexible plastic tube.

6. A dispenser as recited in claim 5, wherein each of said openings in the container is equipped with a fitting that connects said opening and places said opening in liquid communication with one of said conduits.

7. A dispenser as recited in claim 6, wherein each of said openings in the lower plate is equipped with a fitting that connects said opening and places said opening in liquid communication with one of said conduits at the distal end thereof.

8. A dispenser as recited in claim 2, wherein the first and second pinch rollers of said regulating assembly are supported by the side support bars of said support structure and are oriented substantially parallel to said front and rear support bars.

9. A dispenser as recited in claim 8, wherein the first and second pinch rollers are moved between the open position and the closed position by a toggle arrangement, said toggle arrangement being operably and pivotally connected to the rear support bar of said support structure.

10. A dispenser as recited in claim 9, wherein the toggle arrangement includes a hinge that has a front section and a rear section, the rear section of said hinge being operably and pivotally connected to the rear support bar of said support structure, the front and rear sections of said hinge being pivotally secured to one another and pivoting relative to one another along a pivot axis that is substantially parallel to the axis of rotation of said pinch rollers, and the front section of said hinge being adapted to abut said second pinch roller.

11. A dispenser as recited in claim 10, wherein the toggle arrangement further includes a handle that is rigidly secured to the rear section of said hinge such that, when a downward force is applied to said handle, the rear and front sections of the hinge are forced into a flat configuration, thereby causing a lateral force to be applied against the second pinch roller, thereby moving said first and second pinch roller into said closed position.

12. A dispenser as recited in claim 11, wherein said first and second pinch rollers are biased into an open position by one or more springs.

13. A dispenser as recited in claim 12, and further including an adjustment bar and an adjustment rod, said adjustment bar being oriented parallel to and intermediate the front and rear support bars and restricting movement of said pinch rollers toward the front support bar of said dispenser, said adjustment rod being threaded through and extending from said front support bar, passing through an opening defined by said adjustment bar, and having a distal end adapted to abut said first roller, wherein rotation of said adjustment rod causes said adjustment rod to press against the said first pinch roller, adjusting the position of said first pinch roller relative to said second pinch roller.

14. A dispenser as recited in claim 1, wherein said first and second pinch rollers are biased into an open position by one or more springs.

* * * * *